United States Patent

Corn

[11] Patent Number: 5,836,916
[45] Date of Patent: Nov. 17, 1998

[54] COMBINED SPINAL EPIDURAL DEVICE

[75] Inventor: Stephen B. Corn, Sharon, Mass.

[73] Assignee: Children's Medical Center Corporation, Boston, Mass.

[21] Appl. No.: 614,369

[22] Filed: Mar. 12, 1996

Related U.S. Application Data

[60] Provisional application No. 60/004,844, Oct. 5, 1995.

[51] Int. Cl.⁶ ................................................. A61M 5/178
[52] U.S. Cl. ........................... 604/158; 604/164; 604/264
[58] Field of Search .................................... 604/158–167, 604/264, 256, 272–274; 606/184

[56] References Cited

U.S. PATENT DOCUMENTS

| | | | |
|---|---|---|---|
| 4,074,714 | 2/1978 | Binard et al. | 128/218 |
| 4,142,525 | 3/1979 | Binard et al. | 128/218 |
| 4,314,555 | 2/1982 | Sagae | 604/167 |
| 4,338,934 | 7/1982 | Spademan | 604/167 |
| 4,349,023 | 9/1982 | Gross | 604/164 |
| 4,518,383 | 5/1985 | Evans | 604/51 |
| 4,808,157 | 2/1989 | Coombs | 604/44 |
| 4,846,799 | 7/1989 | Tanake et al. | 604/158 |
| 5,026,350 | 6/1991 | Tanaka et al. | 604/158 |
| 5,085,631 | 2/1992 | Leighton | 604/28 |
| 5,100,390 | 3/1992 | Lubeck et al. | 604/158 |
| 5,106,376 | 4/1992 | Mononen et al. | 604/164 |
| 5,163,901 | 11/1992 | Eldor | 604/44 |
| 5,279,570 | 1/1994 | Dombrowski et al. | 604/164 |
| 5,306,239 | 4/1994 | Gurmarnik et al. | 604/51 |
| 5,312,375 | 5/1994 | Gurmarnik | 604/264 |
| 5,330,434 | 7/1994 | McFarlane | 604/164 |
| 5,480,389 | 1/1996 | McWha et al. | 604/165 |
| 5,613,956 | 3/1997 | Pattersone et al. | 604/256 |

OTHER PUBLICATIONS

Holmström, Björn, et al. (1995) "Risk of Catheter Migration During Combined Spinal Epidural Block: Percutaneous Epiduroscopy Study," *Anesthesia Analog* 80: 747–53.

Joshi, G.P., and McCarroll, S.M. (1994) "Evaluation of Combined Spinal–Epidural Anesthesia Using Two Different Techniques," *Regional Anesthesia* 19(3): 169–174.

Urmey, William F., et al. (1995) "Combined Spinal–Epidural Anesthesia for Outpatient Surgery," *Anesthesiology* 83(3): 528–534.

*Primary Examiner*—Wynn Wood Coggins
*Assistant Examiner*—Deborah Blyveis
*Attorney, Agent, or Firm*—Thomas J. Engellenner; David A. Lane, Jr.; Lahive & Cockfield, LLP

[57] ABSTRACT

An adapter element joins and stabilizes cooperating needle sets, such as epidural and spinal needles. The adapter element is particularly useful in combined spinal epidural anesthesia delivery techniques in which the adapter element is mated to the proximal portion of an epidural needle and a spinal needle can be inserted through and supported by an internal channel formed within the adapter element.

12 Claims, 2 Drawing Sheets

COMBINED SPINAL EPIDURAL DEVICE

BACKGROUND OF THE INVENTION

This application is based upon and claims priority from U.S. Provisional Patent Application Ser. No. 60/004,844, filed on Oct. 5, 1995 and entitled "Combined Spinal Epidural Device."

The invention relates to a combined spinal epidural anesthesia delivery device that is reliable and easy to use.

Epidural and spinal anesthesia are well-known anesthetic techniques. Epidural anesthesia is administered through an epidural catheter placed through an epidural needle into the epidural space of a patient. Similarly, during the placement of traditional spinal anesthesia, a spinal anesthesia needle is secured within the skin, the subcutaneous tissue, and the ligamentous structures of the back.

Recently, a combined spinal-epidural (CSE) technique has gained widespread use in the clinical setting. The CSE technique is described, for example, by Urmey et al, *Anesthesiology*, 83:528–534 (1995) and by Joshi et al, *Regional Anesthesia*, 19(3):169–174 (1994). The CSE technique places a spinal needle within the lumen of the epidural needle for spinal anesthetic delivery. One drawback to the CSE technique is that the needle-to-needle relationship of the epidural and spinal needles does not provide sufficient stability of the spinal needle during placement of the anesthetic. Further, the spinal needle used for the currently known CSE technique is longer and heavier than the standard spinal needle. The spinal needle used in current CSE techniques is also placed a further distance from the patient's back, as compared to traditional spinal anesthesia techniques, thus causing difficulty in stabilizing the spinal and epidural needles within the patient's back. As a result of such a lack of stability, movements of the spinal needle can easily occur and lead to failure of this anesthetic technique.

U.S. Pat. No. 5,312,375 describes a device for securing a spinal needle to an introducer needle via a thumbscrew.

In response to such problems, investigators have developed methods of securing the spinal and epidural needles during CSE techniques. Such stabilizing devices tend to be cumbersome and could possibly lead to further needle disruption. Another drawback of such stabilizing devices is that they tend to be rather expensive and/or the manner in which they are to be used is not intuitively obvious. A further disadvantage of such stabilizing devices is that they tend to require that the anesthesiologist manipulate them in a manner in which the anesthesiologist is not accustomed. Such manipulations may themselves lead to needle displacement. Also, the tactile sensation of passing the spinal needle through the firm ligaments and membranes of a patient's back, a sensation that is useful to the anesthesiologist in placing the spinal anesthesia needle (known as the "dural pop"), is not present when existing CSE stabilizing devices are utilized.

Accordingly, there exists a need for a simple, inexpensive and easy-to-use CSE device that stabilizes the spinal needle within the epidural needle during performance of the combined spinal epidural technique. A further advantage would be to provide such a device that restores the familiar sensation afforded by the passing of a spinal needle through the ligamentous structures of the back and ultimately through the dura mater, yielding the "dural pop."

It is thus an object of the invention to provide an apparatus that enables efficient and effective implementation of combined spinal epidural anesthesia delivery techniques using standard epidural and spinal needles. Another object is to provide a safer and more reliable technique for implementing combined spinal epidural anesthesia delivery. A further object is to provide an adapter element that facilitates combined spinal epidural anesthesia delivery techniques. A further object is to provide an adapter element that enables cooperating needle sets to be used effectively in a medical procedure. These and other objects will be apparent to those having ordinary skill in the art upon reading the disclosure that follows.

SUMMARY OF THE INVENTION

The present invention provides a kit for joining and stabilizing cooperating needles that are to be inserted within a patient's body. Cooperating needles are those that are used together such that one needle is passed through the lumen of the other needle.

In one example, the kit is a combined spinal epidural anesthesia delivery kit or system. In this embodiment the kit includes an epidural anesthesia delivery needle and a spinal anesthesia delivery needle, each having an inner lumen. The spinal anesthesia delivery needle has an outer diameter that is smaller than the diameter of the inner lumen of the epidural needle. The kit also includes an adapter element that facilitates the connection and stabilization of the spinal needle within the epidural needle. The adapter element includes an external housing having proximal and distal ends, and an internal channel that extends within the external housing from the proximal to the distal end thereof. The internal channel has a diameter that decreases in the direction from the proximal end to the distal end. Preferably, the internal channel is substantially conical or funnel-shaped. The distal end of the adapter element has an inner diameter that is sufficient to mate with a proximal hub of a cooperating needle such as an epidural needle. The shape of the internal channel, and particularly the decreasing diameter of the inner channel from the proximal to distal end, is advantageous because it helps to guide one needle, such as a smaller diameter spinal needle, accurately through the adapter element and into the inner lumen of the other needle (e.g., an epidural needle).

The adapter element further includes a cover that is associated with the external portion of the proximal end thereof. Preferably, the cover is positioned adjacent to the proximal end of the internal channel. One needle from a cooperating needle set, e.g., a spinal needle, must pass through the cover to gain access to the internal channel and eventually to the lumen of the epidural needle. The cover helps to impart support and stability to the needle that passes therethrough.

The cover may be in the form of a puncturable membrane having no preformed access port defined therein. The puncturable membrane is adapted to be penetrated by a spinal needle, thus allowing the spinal needle to traverse the internal channel and eventually to gain access to the inner lumen of the epidural needle. The puncturable membrane is made of an elastomeric material, such as a latex, that is able to maintain its integrity after puncture by the spinal needle and also to lend support and stability to the spinal needle as it is passed through the assembly.

In another embodiment the cover includes a preformed access port through which the spinal needle may pass to access the internal channel and the lumen of the epidural needle. Such a cover may be made of a puncturable or non-puncturable material. The diameter of the port should be sufficient to enable a suitable needle to pass therethrough, but the tolerance should be sufficiently tight to enable the cover (and the port) to provide support and stability to the needle as it traverses the assembly.

The distal end of the adapter element preferably has a configuration and dimensions that allow it to be joined to the hub connector at the proximal end of an epidural needle. The adapter element mates with the epidural needle in a frictional fit, a threaded connection, or a luer lock connection. In one embodiment the distal end of the internal channel can protrude from the distal end of the housing by a distance of approximately 0.1 to 0.5 mm. Alternatively, the distal end of the internal channel can be recessed within the distal end of the adapter element. The distal end of the internal channel preferably is aligned with the lumen of the epidural needle.

DETAILED DESCRIPTION OF THE INVENTION

The invention provides a novel and useful device and kit for joining and stabilizing cooperating needles that are to be inserted into a patient's body. Cooperating needles, as the term is used herein, refers to needles that typically are used together such that one needle is passed through the lumen of the other needle. One example of a cooperating needle set is a spinal needle and an epidural needle as used in a combined spinal epidural anesthesia delivery system. Although the invention is described herein with respect to cooperating spinal and epidural anesthesia delivery needles, it is understood that the invention is equally applicable to other cooperating needle sets.

The invention provides an assembly for joining and stabilizing cooperating needles, such as spinal and epidural anesthesia delivery needles as used in a combined spinal epidural anesthesia delivery system. The assembly provided by the present invention is reliable and easy to use. One particular advantage of this assembly is that it utilizes a novel adapter element that stabilizes a smaller needle, such as a spinal anesthesia delivery needle, that is inserted within the lumen of a larger needle, such as an epidural anesthesia delivery needle. Another advantage is that the assembly enables an anesthesiologist to perceive the tactile sensation, or "dural pop," that is common when a spinal needle passes through the ligamentous structures and the dura mater of a patient's back.

Figure 1:
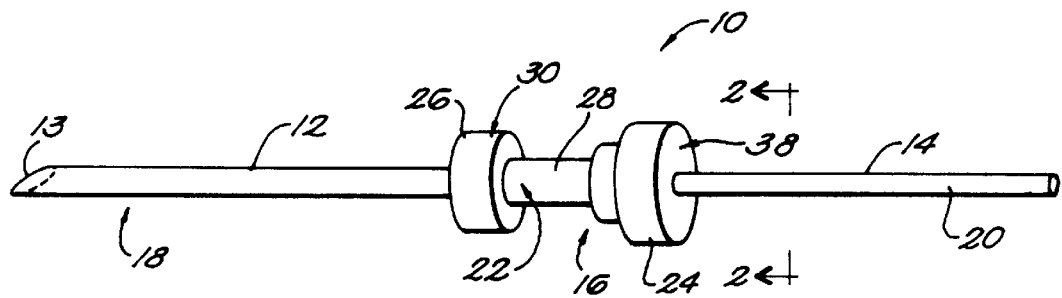
FIG. 1 is a schematic illustration of the cooperating needle assembly of the invention.
Figure 1A:
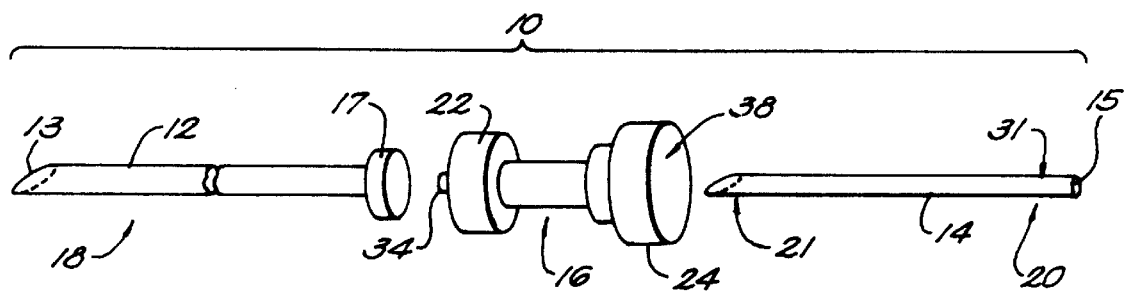
FIG. 1A is an exploded view of the assembly shown in FIG. 1.
Figure 2:
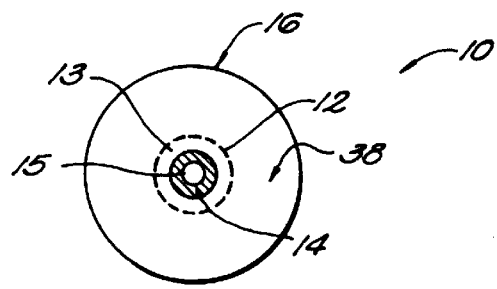
FIG. 2 is a sectional view, at lines 2—2, of the assembly shown in FIG. 1.

FIGS. 1, 1A and 2 illustrate a cooperating needle assembly 10 in which two needles 12, 14 are joined and stabilized by adapter element 16. The assembly 10 has a distal end 18, represented by the first needle 12, and a proximal end 20, represented by the second needle 14.

As illustrated, the first needle 12 has a diameter that is greater than the diameter of second needle 14. The first needle 12 also has an inner lumen 13, the diameter of which is greater than the outer diameter of second needle 14. The second needle 14 also includes an inner lumen 15.

As noted above, the first and second needles can be any type of cooperating needle set. For purposes of describing the present invention, the first needle will be referred to as an epidural needle while the second needle will be referred to as a spinal needle. Suitable epidural needles are those that are well known in the art and that are in standard use for the delivery of epidural anesthesia. Such epidural needles have a length of approximately 8–16 cm with an outer diameter of about 17 gauge and a lumen inner diameter that is sufficient to accomodate a spinal needle. A suitable epidural needle also includes a proximal hub connector 17 which has an outside diameter of about 5–6 mm and an inside diameter of about 4–5 mm. Suitable spinal needles are also of a type that are well known in the art in standard use for the delivery of spinal anesthesia. Such spinal needles have a length of approximately 8–24 cm and an outer diameter that is small enough to fit within the lumen of the epidural needle. Generally, the outer diameter of the spinal needle is about 22 to 27 gauge.

Figure 3:
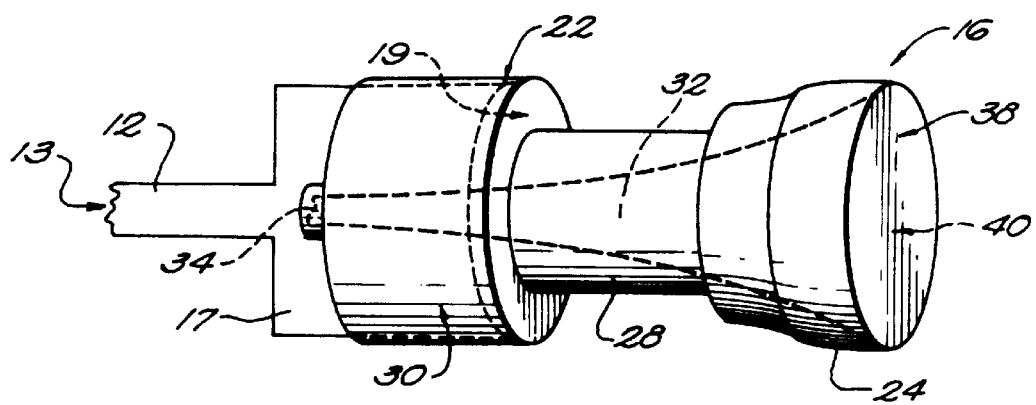
FIG. 3 is a side perspective view of an adapter element useful with the assembly of the invention joined to an eppidural needle.
Figure 4:
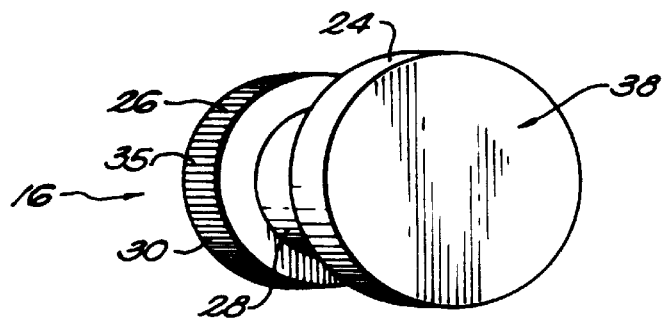
FIG. 4 is a perspective view of one embodiment of an adapter element useful with the assembly of the invention.
Figure 5:
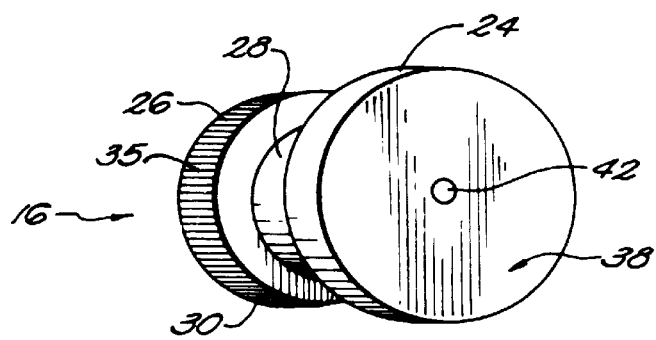
FIG. 5 is a perspective view of another embodiment of an adapter element useful with the assembly of the invention.

As illustrated in FIGS. 1–5, the adapter element 16 has an external housing 22 with proximal and distal ends 24, 26. A proximal end 24 of adapter element 16 may generally be of a cylindrical shape having a diameter that is greater than the diameter of a central portion 28 of adapter 16. Similarly, the distal end 26 of adapter 16 includes an annular rim 30, which also may have a diameter that is greater than the diameter of central portion 28. As best illustrated in FIG. 3, an internal channel 32 is disposed within adapter element 16. The internal channel may have a diameter that tapers such that it is greater at a proximal end 24 of the adapter and lesser at a distal end 26 of the adapter. Preferably, the channel 32 is substantially conical or funnel-shaped. The widest, most proximal part of the channel has a diameter that is substantially the same as the diameter of the proximal end 24 of adapter element 16.

In one embodiment, distal end 34 of internal channel 32 slightly protrudes from the distal end 26 of adapter element 16 as shown in FIG. 3. Alternatively, distal end 34 of internal channel 32 does not protrude from the distal end 26 of adapter element 16, but is instead recessed within the distal end 26 of the adapter element. Even in the recessed position the distal end 34 of the internal channel 32 remains accessable to and in alignment with the lumen 13 of needle 12.

The adapter element 16 may be used to join cooperating needles to form a combined needle assembly 10, as shown in FIG. 1. The assembly is useful in that the adapter element is able to provide support and stability for a second needle 14 (e.g., a spinal needle) while it is inserted within the lumen 13 of the first needle 12 to access a desired region of a patient's body. Any movement of the proximal end 31 of the spinal needle 14 can result in movement of the distal end 21 of the spinal needle which, in an operative position, is disposed within the cerebrospinal fluid (CSF) of a patient and held in place by the patient's dura mater. It is possible that any such movement can cause the spinal needle to be displaced from its desired position within the CSF and thus compromise the proper delivery of the spinal anesthetic.

The proximal end 24 of the adapter element 16 preferably includes a cover 38, or a membrane, which is positioned adjacent to the proximal opening 40 of the internal channel 32. In one embodiment the cover 38 is made of an elastomeric, puncturable membrane. The membrane is preferably essentially self-sealing such that when a needle 14 penetrates the membrane the membrane maintains its integrity and applies a force to the outside wall of the needle 14 helping to maintain the positional stability of the needle.

In another embodiment, the cover may include a preformed port 42 through which needle 14 can be inserted. The port 42 preferably has dimensions suitable to enable spinal needle 14 to pass therethrough. However, tolerance should be relatively small (e.g., 0.001 to 0.005 inch) to enable the needle 14 to be supported and positionally stabilized by the cover 38 and port 42. A resilient, elastomeric seal, such as an 0-ring or gasket (not shown), may be disposed adjacent the port 42 to maintain suitable stabilizing forces on needle 14 as it traverses the port.

The cover or membrane 38 can be made from a variety of synthetic and/or natural elastomeric polymers that are well known in the art. Examples of suitable polymers include various natural or synthetic latex and elastomeric polymers.

The dimensions of the adapter element can vary depending upon the requirements of a given application. One of ordinary skill in the art can, without undue experimentation, readily design an adapter element having the appropriate dimensions. Preferably, the adapter element has a length in the range of about 5 to 20 mm, and most preferably about 10 mm. The diameter of the proximal end 24 and the distal end 26 of the adapter element 16 is in the range of about 5 to 10 mm while the diameter of the central portion 28 of the adapter element 16 is approximately 4 to 8 mm. The diameter of the internal channel 32, at its widest end adjacent to proximal end 24 of the adapter element, is approximately equal to the diameter of the proximal end of the adapter element. The diameter of the internal channel tapers in the direction of the distal end of the internal channel. Preferably, the inner diameter of the most distal end 34 of the internal channel 32 is approximately 1–3 mm. The outer diameter of the distal end 26 of adapter element 16 is sufficient to mate with the hub connector 17 of needle 12 to which it is to be joined. Preferably, this diameter is in the range of about 3–6 mm.

The adapter clement preferably fits over the outer diameter of the proximal hub 17 of an epidural needle to effect a threaded or luer lock connection. In such embodiments, the external wall of the hub 17 and the internal wall of the distal end 26 of adapter element 16 have the necessary structures to accomodate such a connection. Further, a frictional fit connection between the adapter element 16 and the proximal hub 17 of needle 12 is typically effected by configuring the distal end 26 of adapter 16 such that it is able to fit internally within the hub 17.

It is understood that the dimensions and shape of adapter element 16 may vary. In one embodiment (not shown) the adapter element is of a relatively short length and does not include intermediate section 28. In such an embodiment the proximal end of internal chamber 32 and cover 38 are disposed only about 1 to 3 mm distally of the proximal hub 17 of needle 12.

As shown in FIG. 1, the adapter element 16 may be joined to a cooperating needle set as follows. The distal end 26 of adapter element 16 is mountable to the proximal hub connector 17 of the epidural needle 12 by a suitable means. In a preferred embodiment the distal end 26 of the adapter element 16 mates with the proximal hub connector 17 of needle 12 through a frictional fit, a luer lock connection, or a threaded connection. Preferably, the distal end 34 of the internal channel 32 is aligned with the inner lumen 13 of needle 12.

The external housing 22 of adapter element 16 includes a distal, annular rim 30 that enables the adapter element to be manipulated for attachment to and removal from the epidural needle. The annular rim 30 may include ridges 35 to aid in the gripping of the device. A base wall 19 of adapter element 16 prevents the adapter element from being positioned too deeply within the epidural needle by abutting the proximal end 17 of needle 12. The needle 14 (e.g., a spinal needle) may then be inserted through the proximal end 24 of the adapter element 16 such that it traverses the internal channel 32 of the adapter element and enters the inner lumen 13 of the needle 12 (e.g., an epidural needle.) The configuration of the internal channel is such that it easily and accurately guides the spinal needle into a position within the inner lumen of the epidural needle.

The claimed invention is particularly useful in the administration of combined spinal epidural anesthesia delivery techniques. In such an application, the assembly of the invention can be used as follows. The epidural space is located by an anesthesiologist, using an epidural needle, in the usual fashion. Once the epidural needle is properly placed within the patient, the adapter element is attached to the proximal end of the epidural needle such that the distal end of the internal channel mates within the lumen of the epidural needle. The spinal needle is then inserted through the cover, or membrane, of the adapter element into the internal channel of the adapter element. The spinal needle is advanced through the lumen of the epidural needle until the "dural pop" is felt, indicating that the spinal needle has passed through the ligaments of the patient's spine. Once the "dural pop" is felt, the anesthesiologist can check for cerebrospinal fluid (CSF) and placement of the spinal anesthetic can proceed in the usual fashion. In this position the spinal needle is held firmly in place by the adapter element. Once the proper dosage of spinal anesthetic is delivered, the spinal needle and the adapter element can be removed as a unit. Thereafter, an epidural catheter can be threaded through the epidural needle, in the typical manner, to administer epidural anesthetic. One of ordinary skill in the art will appreciate that this technique, as applied to combined spinal epidural anesthetic delivery, can be modified for use with other cooperating needle sets. Alternatively, the adapter element can be pre-assembled upon the spinal needle, and this combination can be attached subsequently to the epidural needle.

Those of ordinary skill in the art will recognize, or be able to ascertain, using no more than routine experimentation, numerous equivalents to the procedures and systems described herein. Such equivalents are considered to be within the scope of the invention and are covered by the following claims. The content of all references described herein is hereby incorporated by reference.

What is claimed is:

1. A needle joinder kit, comprising:
    a first needle having an inner lumen;
    a second needle having an inner lumen and an outer diameter that is smaller than the inner diameter of the inner lumen of the first needle; and
    an adapter element adapted to facilitate connection and stabilization of the second needle within the first needle, the adapter element having
        a housing with distal and proximal ends,
        an internal channel, disposed within the housing, having an inner diameter that decreases in the direction from the proximal to the distal end, the distal end of the internal channel being matable with the first needle, and
        a cover associated with the proximal end of the housing of the adapter element, adjacent to the internal channel, through which the second needle is inserted to traverse the internal channel and the lumen of the first needle;

the cover including a puncturable membrane for providing positional stability to the second needle when the second needle is inserted into the internal channel.

2. The kit of claim 1 wherein the internal channel is substantially conically shaped having a diameter at its proximal end that is substantially the same as the diameter of the proximal end of the housing, tapering to a smaller diameter at its distal end.

3. The kit of claim 2 wherein the distal end of the internal channel protrudes from the distal end of the housing.

4. The kit of claim 3 wherein the distal end of the internal channel protrudes from the distal end of the housing by a distance of approximately 0.5 to 5 mm.

5. The kit of claim 3 wherein the first needle includes a proximal hub and the outer diameter of the distal end of the internal channel is less than the inner diameter of the proximal hub of the first needle.

6. The kit of claim 1 wherein the puncturable membrane is constructed from a resilient material and engages an outer surface of the inner needle to stabilize the inner needle.

7. The kit of claim 6 wherein the membrane is formed from a material selected from the group consisting of synthetic and natural elastomeric polymers.

8. The kit of claim 1 wherein the adapter element mates with the first needle by frictional engagement of the distal end of the adapter element with a proximal hub of the first needle.

9. The kit of claim 1 wherein the length of the adapter element is approximately 5 to 10 mm.

10. The kit of claim 1 wherein the first needle is an epidural anesthesia delivery needle and the second needle is a spinal anesthesia delivery needle.

11. A needle assembly, comprising:

an outer needle having a proximal hub and defining an internal channel;

a housing including a cover, the housing being attachable to the outer needle; and an inner needle extending through a puncturable membrane and slidably disposable within the internal channel, the puncturable membrane configured to engage an outer surface of the inner needle to stabilize the inner needle and affixed to a proximal end of the housing such that it provides a barrier through which the inner needle must pass, thereby acting as a constraint on the inner needle to reduce inadvertent displacement or movement of the inner needle.

12. A needle joinder kit, comprising:

a first needle having an inner lumen;

a second needle having an inner lumen and an outer diameter that is smaller than the inner diameter of the inner lumen of the first needle; and an adapter element adapted to facilitate connection and stabilization of the second needle within the first needle, the adapter element having a housing with distal and proximal ends, an internal channel disposed within the housing, and a membrane element associated with the proximal end of the housing of the adapter element, adjacent to the internal channel, through which the second needle is inserted to traverse the internal channel and the lumen of the first needle, the membrane element being adapted to stabilize the second needle.

* * * * *